United States Patent
Onuki et al.

(10) Patent No.: US 10,085,797 B2
(45) Date of Patent: Oct. 2, 2018

(54) HIGH-FREQUENCY TREATMENT INSTRUMENT

(71) Applicant: OLYMPUS CORPORATION, Tokyo (JP)

(72) Inventors: Yoshio Onuki, Tokyo (JP); Hiromichi Sakano, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/495,234

(22) Filed: Apr. 24, 2017

(65) Prior Publication Data

US 2017/0224411 A1    Aug. 10, 2017

Related U.S. Application Data

(63) Continuation of application No. PCT/JP2016/066446, filed on Jun. 2, 2016.

(30) Foreign Application Priority Data

Jun. 18, 2015  (JP) ................................ 2015-122944

(51) Int. Cl.
    *A61B 18/14*    (2006.01)
    *A61B 17/00*    (2006.01)
    (Continued)

(52) U.S. Cl.
    CPC .... *A61B 18/1482* (2013.01); *A61B 17/00234* (2013.01); *A61B 1/00071* (2013.01);
    (Continued)

(58) Field of Classification Search
    CPC .... A61B 2018/1412; A61B 2018/1475; A61B 18/1492; A61B 1/015; A61B 1/018;
    (Continued)

(56) References Cited

U.S. PATENT DOCUMENTS

2001/0039413 A1* 11/2001 Bowe ................ A61M 25/0041
                                                                 604/532
2004/0210215 A1   10/2004 Okada
                        (Continued)

FOREIGN PATENT DOCUMENTS

| EP | 2896379 A1 | 7/2015 |
|---|---|---|
| EP | 2910212 A1 | 8/2015 |
| JP | H08-299355 A | 11/1996 |
| JP | 2004-167081 A | 6/2004 |
| JP | 2008-301861 A | 12/2008 |
| JP | 2012-075657 A | 4/2012 |

(Continued)

OTHER PUBLICATIONS

International Search Report dated Aug. 30, 2016 issued in PCT/JP2016/066446.

*Primary Examiner* — Sean W Collins
(74) *Attorney, Agent, or Firm* — Scully, Scott, Murphy & Presser, P.C.

(57) ABSTRACT

A high-frequency treatment instrument including: a sheath formed of a flexible material; an electrode member disposed inside the sheath; a distal-end member having a through-hole through which the electrode member passes; and a liquid supply means supplying liquid towards the front side via a flow path in the sheath, wherein the electrode member includes a rod-shaped electrode portion movably passing through the through-hole, and a large-diameter portion provided at the distal end thereof to have an outer diameter larger than the diameter of the through-hole, the large-diameter portion includes an electrode hole passing therethrough, between the distal-end member and the large-diameter portion, there is provided a buffer member that seals the periphery of a space between the distal-end member and the large-diameter portion.

3 Claims, 5 Drawing Sheets

(51) Int. Cl.
*A61B 18/00* (2006.01)
*A61B 1/00* (2006.01)

(52) U.S. Cl.
CPC ............... *A61B 2017/00269* (2013.01); *A61B 2017/00296* (2013.01); *A61B 2018/0063* (2013.01); *A61B 2018/00601* (2013.01); *A61B 2018/1475* (2013.01); *A61B 2218/002* (2013.01)

(58) Field of Classification Search
CPC ........ A61B 2218/002; A61B 2218/006; A61B 2017/00269; A61B 2017/00296; A61B 2017/0034; A61B 17/00234; A61B 1/00071; A61B 1/00137
See application file for complete search history.

(56) References Cited

U.S. PATENT DOCUMENTS

| | | |
|---|---|---|
| 2007/0239187 A1* | 10/2007 | Brunnett ............ A61B 17/1622 606/172 |
| 2008/0195094 A1 | 8/2008 | Okada |
| 2014/0207134 A1 | 7/2014 | Wake |
| 2014/0288554 A1 | 9/2014 | Okada |

FOREIGN PATENT DOCUMENTS

| | | | | |
|---|---|---|---|---|
| JP | WO 2014042039 A1 * | 3/2014 | ............ | A61B 18/14 |
| JP | 5646788 B2 | 12/2014 | | |
| JP | 5654181 B2 | 1/2015 | | |

* cited by examiner

HIGH-FREQUENCY TREATMENT INSTRUMENT

CROSS-REFERENCE TO RELATED APPLICATIONS

This application is a Continuation Application of International Application No. PCT/JP2016/066446 filed on Jun. 2, 2016, which claims priority to Japanese Application No. 2015-122944 filed on Jun. 18, 2015. The Contents of International Application No. PCT/JP2016/066446 and Japanese application No. 2015-122944 are hereby incorporated herein by reference in their entirety.

TECHNICAL FIELD

The present invention relates to a high-frequency treatment instrument.

BACKGROUND ART

In the related art, there is a known high-frequency treatment instrument in which a high-frequency current is applied so as to treat biological tissue, such as a mucous membrane (for example, see PTL 1).

In this high-frequency treatment instrument, a rod-shaped electrode portion is disposed by being inserted in a through-hole in an electrically insulating support member provided at the distal end of a sheath, so as to be advanceable/retractable in the axial direction. A wire that transmits a tensile force and that supplies the high-frequency current is connected to the proximal end of the rod-shaped electrode portion, and the rod-shaped electrode portion is advanced and retracted by operating an operating portion disposed at the proximal end of the sheath. In addition, an electrically insulating large-diameter portion is provided at the distal end of the rod-shaped electrode portion, and the large-diameter portion is provided with a through-hole that passes therethrough from the proximal end to the distal end.

Accordingly, in a state in which the rod-shaped electrode portion is moved to the extreme proximal end so that the large-diameter portion comes into close contact with the support member, liquid sent through the sheath can be discharged toward the front of the large-diameter portion via a gap between the through-hole in the support portion and the rod-shaped electrode portion and via the through-hole in the large-diameter portion.

CITATION LIST

Patent Literature

{PTL1} Publication of Japanese Patent No. 5654181

SUMMARY OF INVENTION

One aspect of the present invention provides a high-frequency treatment instrument comprising: an elongated cylindrical sheath formed of a flexible material; an electrode member that is disposed inside the sheath so as to be advanceable/retractable in a longitudinal direction thereof and to which a high-frequency current is supplied; a distal-end member that is disposed at a distal end side of the sheath and that has a through-hole through which the electrode member passes; and a liquid supply means that supplies liquid towards a front side in the longitudinal direction of the sheath via a flow path that is connected to a proximal end side of the sheath and that is formed in the sheath and via a gap between the through-hole and the electrode member, which communicates with the flow path, wherein the electrode member includes a rod-shaped electrode portion that passes through the through-hole in a movable manner, and a large-diameter portion that is provided at a distal end of the rod-shaped electrode portion, that is formed of an insulating material, and that has an outer diameter larger than an diameter of the through-hole, the large-diameter portion includes an electrode hole that passes through the large-diameter portion in the longitudinal direction, and the high-frequency treatment instrument comprises, between the distal-end member and the large-diameter portion, a buffer member which can be elastically deformed in the longitudinal direction when the electrode member is moved to the most proximal end side and which seals a periphery of a space formed between the distal-end member and the large-diameter portion throughout the entire circumference thereof, wherein the space communicates with the through-hole and the electrode hole.

DESCRIPTION OF EMBODIMENTS

A high-frequency treatment tool 1 according to a first embodiment of the present invention will be described below with reference to the drawings.

Figure 1:
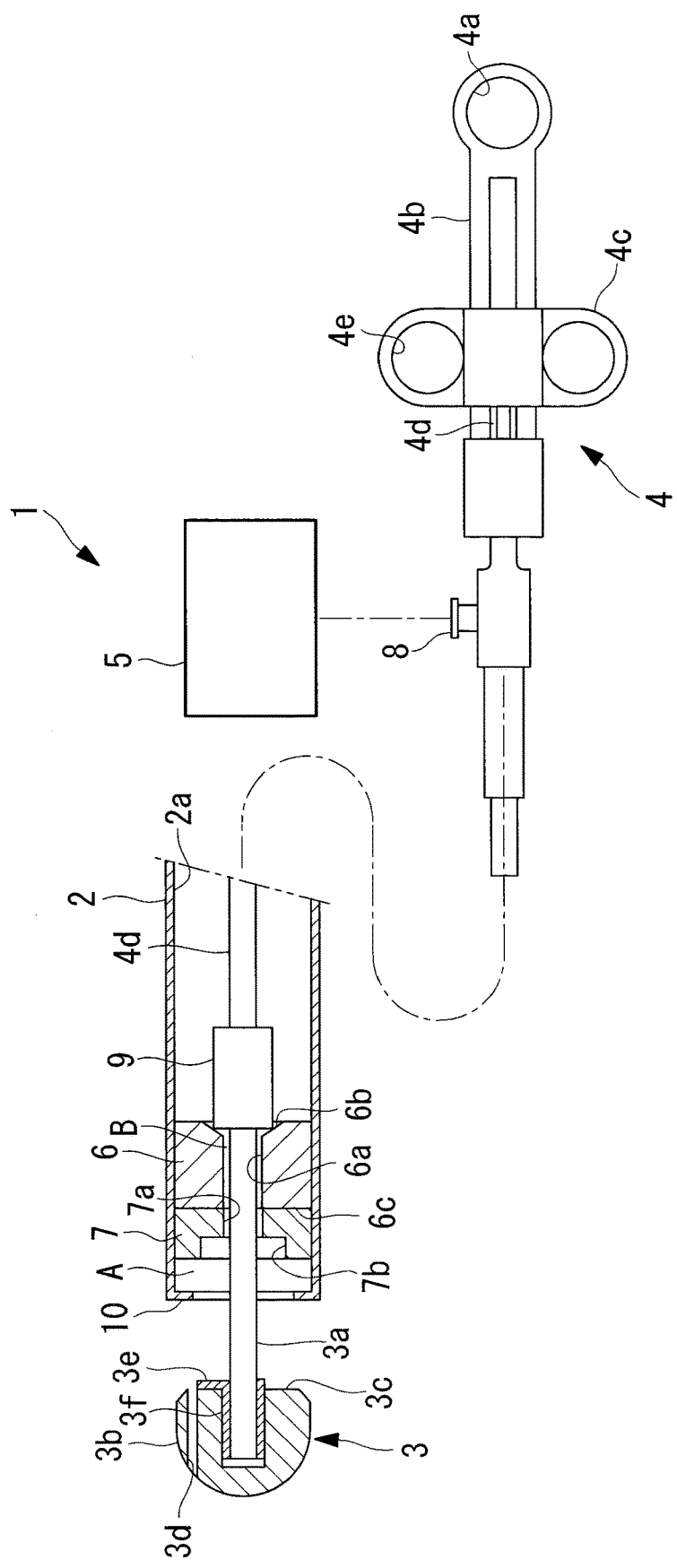
FIG. 1 is a diagram showing the overall configuration of a high-frequency treatment instrument according to a first embodiment of the present invention, in which a distal end portion is magnified and another portion is omitted.

The high-frequency treatment instrument 1 according to this embodiment is, for example, a treatment tool whose distal end is introduced inside a body via a channel provided in an insertion portion of an endoscope, and as shown in FIG. 1, includes a sheath 2 formed in an elongated cylindrical shape that can be inserted into the channel and having flexibility; an electrode member 3 that can be advanced/retracted at the distal end of the sheath; an operating portion 4 that pushes and pulls the electrode member 3 at a proximal end of the sheath; a wire (tensile-force transmitting member) 4d that transmits a tensile force generated by the operating portion 4 to the electrode member 3; and a liquid supply means 5 for discharging liquid from the distal end of the sheath 2 via an inner hole (flow path) 2a in the sheath 2.

Figure 2:
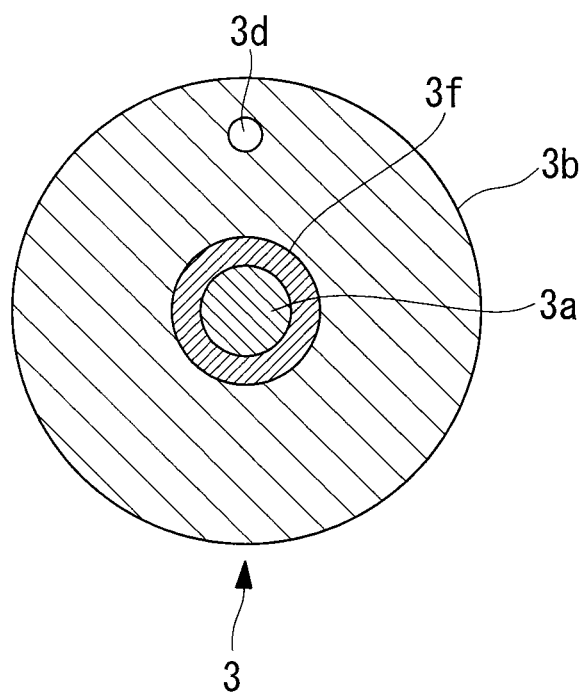
FIG. 2 is a transversal sectional view showing a large-diameter portion of the high-frequency treatment instrument in FIG. 1.

A plug-shaped distal-end member 6 is fixed at the distal end of the sheath 2 so as to close the inner hole 2a. As shown in FIG. 2, the distal-end member 6 is provided with a through-hole 6a passing therethrough in the longitudinal direction and through which the electrode member 3 movably passes. The through-hole 6a has a circular cross-section and is provided, at the base end thereof, with a tapered inner surface 6b that has a conical inner surface and that narrows towards the distal end.

An annular insulating tip 7 formed of an electrically insulating material (for example, ceramic) is provided at a distal end side of the distal-end member 6. A through-hole 7a having an opening diameter that matches that of the through-hole 6a in the distal-end member 6 and a recessed section 7b having an opening diameter larger than that of the through-hole 7a are provided in the insulating tip 7, and the insulating tip 7 is fixed to a distal-end surface 6c of the distal-end member 6 so that the recessed section 7b opens towards the front.

The electrode member 3 is formed of a conductive material. The electrode member 3 includes: the rod-shaped electrode portion 3a having a circular cross-section with a diameter sufficiently smaller than that of the through-hole 6a; and the large-diameter portion 3a which is hemispherical and is fixed to the distal end of the rod-shaped electrode portion 3a. In addition, a stopper portion 9 that has a cross-sectional shape having a larger diameter than the rod-shaped electrode portion 3a and that is formed in a circular rod shape concentric with the rod-shaped electrode portion 3a is fixed to a proximal end side of the rod-shaped electrode portion 3a.

Then the electrode member 3 is moved to the most distal end, the stopper portion 9 abuts against the tapered inner surface 6b of the distal-end member 6, so as to restrict the advancing movement of the electrode member 3 beyond that point.

The stopper portion 9 is a member that mechanically and electrically connects the wire 4d and the electrode member 3. The tensile force transmitted by the wire 4d is transmitted to the electrode member 3 via the stopper portion 9, so that the electrode member 3 can be pulled towards the proximal end. In addition, a high-frequency current transmitted by the wire 4d is also supplied to the electrode member 3 via the stopper portion 9, so that tissue can be cut or the like.

The large-diameter portion 3b has an outer diameter substantially equal to the outer diameter of the insulating tip 7 and is provided, at the proximal end thereof, with a flat portion 3c that is perpendicular to the longitudinal axis of the rod-shaped electrode portion 3a. An electrode hole 3d that passes through the large-diameter portion 3b in the longitudinal direction of the rod-shaped electrode portion 3a is provided in the large-diameter portion 3b. In the example shown in FIG. 2, the electrode hole 3d is provided at one place.

The large-diameter portion 3b is provided with an auxiliary electrode 3f having rod-shaped portions 3e that are arranged at equal intervals in the circumferential direction and that extend, in a radiating pattern, in the radial direction of the sheath 2. The rod-shaped electrode portion 3a passes through the cylindrical inner space and is fixed to the auxiliary electrode 3f. In this configuration, the rod-shaped portions 3e of the auxiliary electrode 3f are in close contact with the flat portion 3c of the large-diameter portion 3b so as not to overlap the electrode hole 3d.

Figure 3:
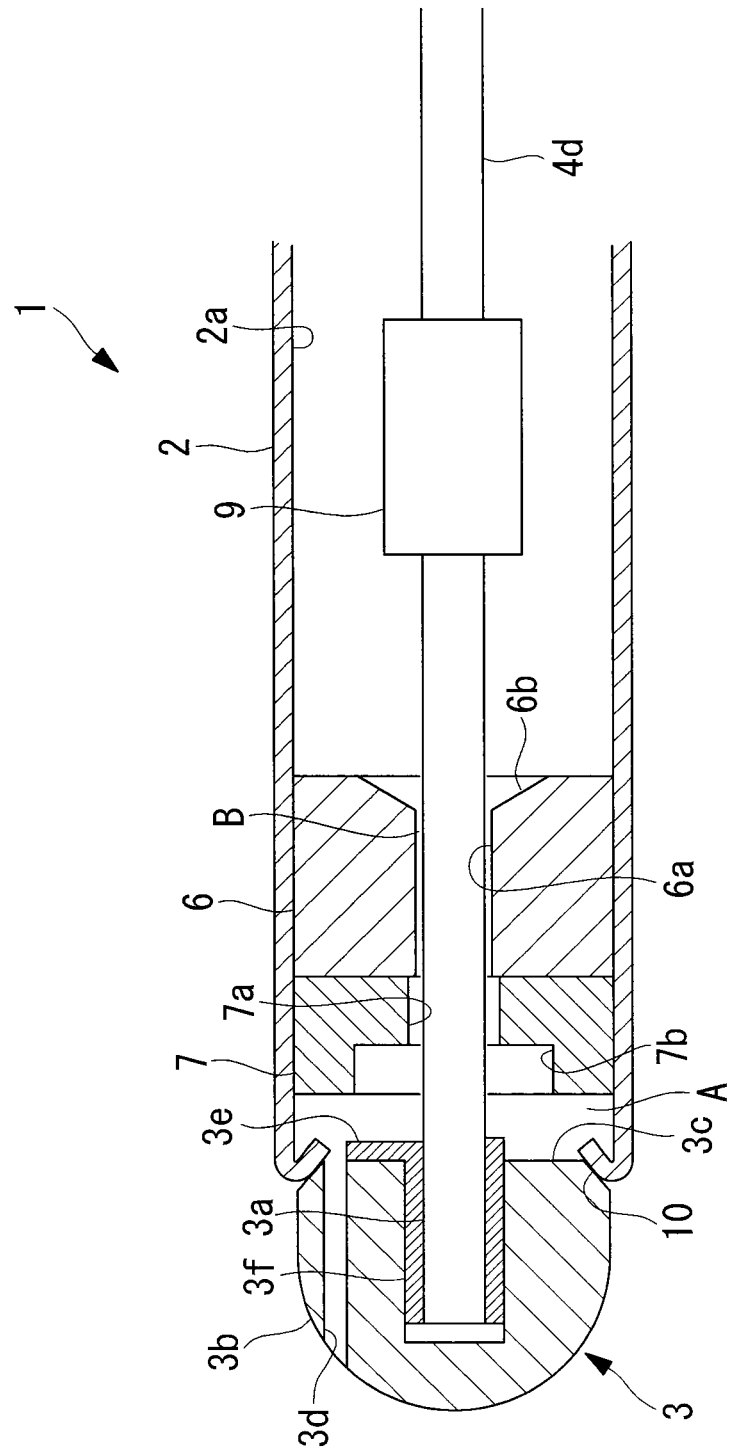
FIG. 3 is a magnified longitudinal sectional view of the distal-end portion, showing a state in which an electrode member in the high-frequency treatment instrument in FIG. 1 is maximally retracted.

In this embodiment, the sheath 2 extends farther towards the distal end side than the insulating tip 7, and the distal end of the sheath 2 is folded inward in the radial direction, throughout the entire circumference thereof, and thereby an inner-flange-shaped buffer member 10 is formed. As shown in FIG. 3, when the electrode member 3 is moved to the most proximal end, the buffer member 10 is brought into close contact, throughout the entire circumference thereof, with the peripheral edge portion of the flat portion 3c at the proximal end of the large-diameter portion 3b, and thereby the periphery of the space A between the large-diameter portion 3b and the insulating tip 7 is sealed. In the state in which the area around the space A is sealed by the buffer member 10, the electrode hole 3d provided in the large-diameter portion 3b communicates with a cylindrical gap B between the through-hole 6a and the rod-shaped electrode portion 3a via the aforementioned space A.

The sheath 2 is formed, for example, of a material having electrical insulating properties and flexibility, such as polytetrafluoroethylene. Accordingly, when an excessive tensile force is applied to the electrode member 3, the flat portion 3c of the large-diameter portion 3b abuts against the buffer member 10, causing it to elastically deform in the longitudinal direction, and thereby the impact generated between them is reduced. Then, due to the elastic restoring force with which the elastic force in the buffer member 10 pushes back the large-diameter portion 3b to the distal end side, the contact properties between the buffer member 10 and the flat portion 3c of the large-diameter portion 3b are improved.

The operating portion 4 includes a handle 4b having a finger-insertion hole attached to the proximal end of the sheath 2, a movable portion 4c provided so as to move in the longitudinal direction of the sheath 2 relative to the handle 4b, and a wire 4d disposed inside the inner hole 2a in the sheath 2 and formed of a conductive material for coupling the movable portion 4c and the electrode member 3. Reference sign 4e in the figure is a finger-insertion hole provided in the movable portion 4c.

When the movable portion 4c is moved to the distal end side of the sheath 2 relative to the handle 4b, a pushing force is transmitted to the electrode member 3 via the wire 4d, and the electrode member 3 is moved in a direction in which it advances relative to the distal-end member 6. When the movable portion 4c is moved to the proximal end side of the sheath 2 relative to the handle 4b, a pulling force is transmitted to the electrode member 3 via the wire 4d, and the electrode member 3 is retracted in a direction in which it is pulled inside the through-hole 6a in the distal-end member 6.

A power supply source (not illustrated) is connected to the proximal end of the wire 4d, so as to supply a high-frequency current to the electrode member 3 via the wire 4d.

The handle 4b is provided with a connection opening 8 that communicates with the inner hole 2a in the sheath 2.

The liquid supply means 5 is a syringe, a pump, or the like that is connected to the connection opening 8, so as to supply a liquid, such as physiological saline, into the inner hole 2a in the sheath 2 via the operation of the liquid supply means 5.

The operation of the thus-configured high-frequency treatment instrument 1 according to this embodiment will be described below.

To perform endoscopic submucosal dissection using the high-frequency treatment instrument 1 according to this embodiment, the operating portion 4 is operated, and in the state in which the electrode member is maximally retracted, as shown in FIG. 3, the sheath 2 is introduced into the body from the distal end side thereof via the channel in the insertion portion of the endoscope, and the distal end is made to protrude from the distal end of the insertion portion in the endoscope.

Accordingly, since the distal-end member 6 disposed at the distal end of the sheath 2 enters the field of view of the endoscope, the operator performs treatment while checking the images captured by the endoscope on a monitor. In the state in which the electrode member 3 is maximally retracted, since only the large-diameter portion 3b of the electrode member 3 is exposed at the distal end of the sheath 2, the electrode member 3 is not inserted deeply into the tissue. Since the large-diameter portion 3b is formed in a hemispherical shape, and the hemispherical portion is disposed at the distal end side, it does not damage the tissue with which it comes into contact.

In this state, the flat portion 3c of the large-diameter portion 3b abuts against the buffer member 10, and the periphery of the space A between the insulating tip 7 and the large-diameter portion 3b is sealed. Therefore, when liquid is supplied via the inner hole 2a in the sheath 2 by the operation of the liquid supply means 5, the liquid can be efficiently discharged straight in front of the large-diameter portion 3b without leaking, via the electrode hole 3d, which is coupled to the cylindrical gap B between the through-hole 6a in the distal end member 6 and the rod-shaped electrode portion 3a, the space A in front of the insulating tip 7, and the space A.

The endoscopic submucosal dissection using the high-frequency treatment instrument 1 according to this embodiment is as follows, when explained following the flow of the procedure. First, an injection needle (not illustrated) is introduced into the body cavity via a channel in the endoscope (not illustrated), and in an endoscopic image displayed on the monitor, a site suspected of being diseased, which must be excised, is injected with physiological saline submucosally, to cause the diseased site to bulge. Next, a high-frequency knife having a conventional needle-shaped electrode is inserted via the channel in the endoscope, and after making an initial incision to form a hole in part of the mucous membrane around the diseased site, the high-frequency knife is removed from the channel.

In this state, assuming a state in which the movable portion 4c is moved to the proximal end with respect to the handle 4b in the operating portion 4 so that the electrode member 3 is moved to the extreme proximal end, the high-frequency treatment instrument 1 according to this embodiment is introduced into the body cavity via the channel in the endoscope. Then, as shown in FIG. 1, the movable portion 4c is moved to the distal end side with respect to the handle 4b in the operating portion 4 so that the electrode member 3 is moved to the extreme distal end side.

When the electrode member is moved to the distal end side, the stopper portion 9 provided at the proximal end of the electrode member 3 abuts against the tapered inner surface 6b of the distal-end member 6 so as to be restricted from moving farther than that point, and the rod-shaped electrode portion 3a enters a state in which it protrudes towards the front of the sheath 2. In this state, the electrode member 3 is inserted into the hole formed in advance by the initial incision, starting from the large-diameter portion 3b.

In this state, the rod-shaped electrode portion 3a is moved in a prescribed incision direction that intersects the longitudinal direction while supplying a high-frequency current to the rod-shaped electrode portion 3a via the wire 4d, and thereby it is possible to excise the mucous membrane around the diseased site.

In this case, because the large-diameter portion 3b provided at the distal end of the electrode member 3 is formed of a material having insulating characteristics, even though the high-frequency current is supplied to the electrode member 3, the tissue with which the large-diameter portion 3b is brought into contact is not incised. Therefore, it is possible to prevent a drawback that the tissue below the mucous membrane is incised.

Also, in the case where bleeding occurs when incising the mucous membrane around the diseased site, the operating portion 4 is operated to move the electrode member 3 to the extreme proximal end, as shown in FIG. 3. Accordingly, the flat portion 3c of the large-diameter portion 3b of the electrode member 3 abuts against the buffer member 10, and the periphery of the space A between the large-diameter portion 3b and the insulating tip 7 is sealed throughout the entire circumference thereof.

In this state, when the liquid supply means 5 is operated to supply liquid into the inner hole 2a in the sheath 2, the supplied liquid is discharged, via the gap B between the through-hole 6a and the rod-shaped electrode portion 3a, towards the front of the large-diameter portion 3b via the electrode 3d, without leaking outward in the radial direction from the space A. Accordingly, the bleeding is washed away to clarify the site where bleeding has occurred, making it possible to facilitate hemostasis treatment.

In this case, with the high-frequency treatment instrument 1 according to this embodiment, when performing the operation of pulling back the electrode member 3 to the extreme proximal end, a large tensile force due to the large pulling force applied to the operating portion 4 is transmitted to the electrode member 3 via the wire 4d. In particular, in an emergency such as when bleeding occurs, since it is necessary to quickly perform hemostasis treatment, the operator may apply a large pulling force.

In addition, the tissue incised in the incision step may be burned onto the rod-shaped electrode portion 3a. At such times, there are cases where the operator moves the movable portion 4c back and forth a plurality of times relative to the handle 4b in the operating portion 4, so that the electrode member 3 is repeatedly advanced and retracted. In this case too, a large pulling force may be applied to the operating portion 4 a plurality of times.

In these cases, with the high-frequency treatment instrument 1 according to this embodiment, the large-diameter portion 3b, when pulled back to the proximal end, abuts against the buffer member 10 forming part of the sheath 2 so as to elastically deform it, and therefore, a direct collision between the large-diameter portion 3b and the insulating tip 7 is avoided, and the impact is reduced. As a result, an advantage is afforded in that it is possible to prevent the drawback that the large-diameter portion 3b falls off the rod-shaped electrode portion 3a or becomes damaged, by a collision due to an excessive tensile force.

When time passes from injection of physiological saline by the injection needle prior to the incision described above, the physiological saline injected below the mucous membrane at the diseased site moves to the peripheral part, and the height of the raised part at the diseased site may be lowered. In such a case too, as shown in FIG. 3, the large-diameter portion 3b of the high-frequency treatment instrument 1 according to this embodiment, in a state where the electrode member 3 has been moved to the extreme proximal end, is pushed against the lower layer in the mucous membrane exposed by the incision, and the liquid supply means 5 is operated, thereby locally injecting additional physiological saline submucosally, so that the diseased site can be made to bulge again.

Thus, with the high-frequency treatment instrument 1 according to this embodiment, at the time of bleeding during incision or at the time of locally injecting additional physiological saline, it is not necessary to remove the high-frequency treatment instrument 1 from the channel in the endoscope, and therefore, an advantage is afforded in that it is possible to shorten the time required for the procedure.

Although the large-diameter portion 3b is formed in a hemispherical shape in this embodiment, instead of this, the large-diameter portion 3b may be formed in a spherical shape, and the spherical surface may be brought into contact with the buffer member 10.

In addition, the number of electrode holes 3d is not limited to a single location, and any number may be provided. In this case, it is preferable to form the electrode holes 3d at equal intervals in the circumferential direction.

In this embodiment, although a sheath formed of a material having electrically insulating properties and elasticity has been illustrated as an example of the sheath 2, an object having a two-layer structure, such as one in which the inner layer is formed of a coil sheath, and the outer layer is formed of a plastic tube, may be employed.

In addition, in this embodiment, the buffer member 10 is formed by folding the distal end portion of the sheath 2 inward in the radial direction. Accordingly, an advantage is afforded in that the buffer member 10 can be formed just by bending the distal end portion of the simple cylindrical sheath 2.

Figure 4:
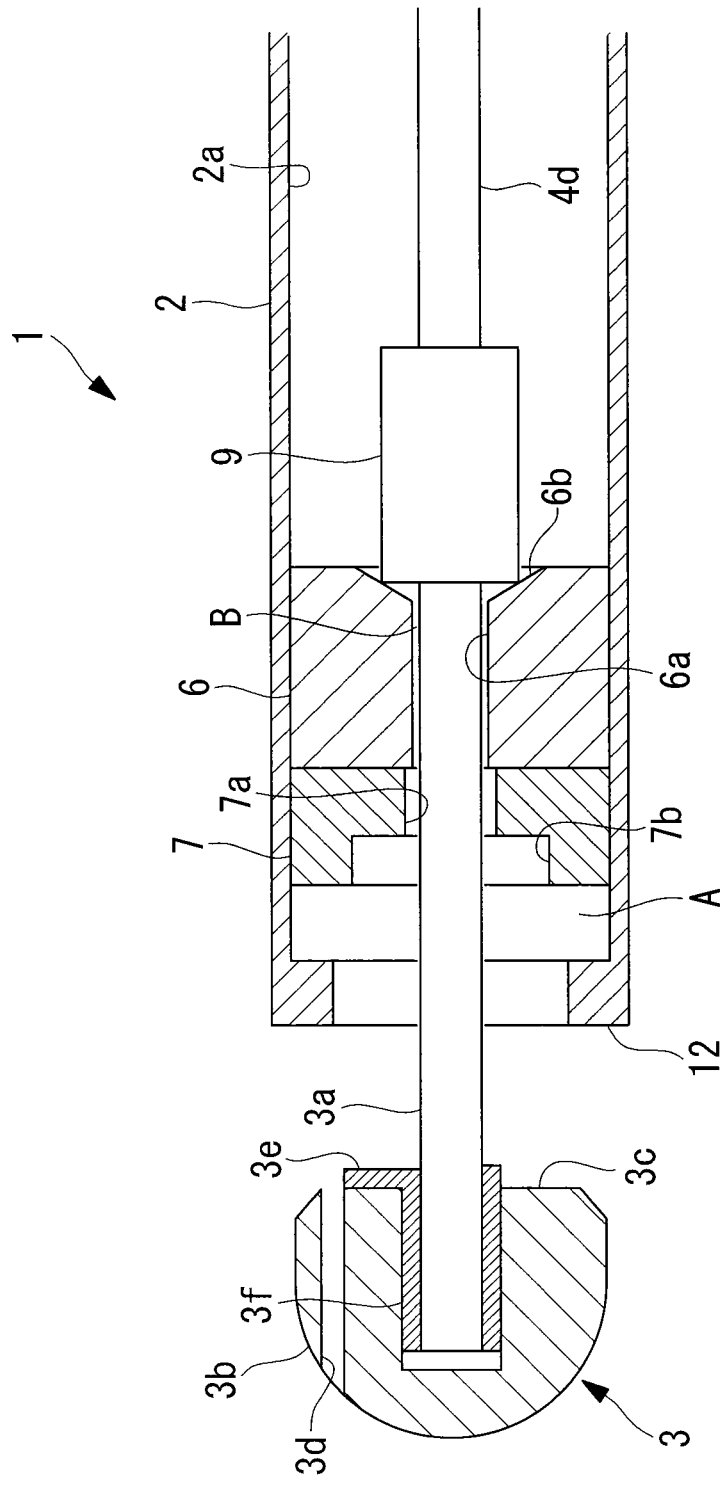
FIG. 4 is a magnified longitudinal sectional view of the distal-end portion showing a modification of the high-frequency treatment instrument in FIG. 1.

Alternatively, as shown in FIG. 4, a buffer member 12 may be formed at the distal end portion of the sheath 2 by a portion that is thicker than the other portions and that protrudes inward in the radial direction. In this case, the buffer member 12 is compressed in the longitudinal direction by being sandwiched between the large-diameter portion 3b and the insulating tip 7, and thereby the impact can be reduced by the elasticity thereof. In addition, bending processing of the distal end portion of the sheath 2 is not required, and it is not necessary to use a separate member for the buffer member 12, thus making it possible to achieve a reduction in the number of parts.

Another way to provide the buffer member 12 is to form the buffer member 12 as a separate member from the distal end portion of the sheath 2. In this case, the buffer member 12 can be provided without performing special processing on the sheath 2.

Next, a high-frequency treatment instrument 20 according to a second embodiment of the present invention will be described below with reference to the drawings.

In the description of this embodiment, parts having the same configuration as those in the high-frequency treatment instrument 1 according to the first embodiment described above are assigned the same reference signs, and a description thereof is omitted.

The high-frequency treatment instrument 20 according to this embodiment differs from the high-frequency treatment instrument 1 according to the first embodiment with regard to a buffer member 21.

Figure 5:
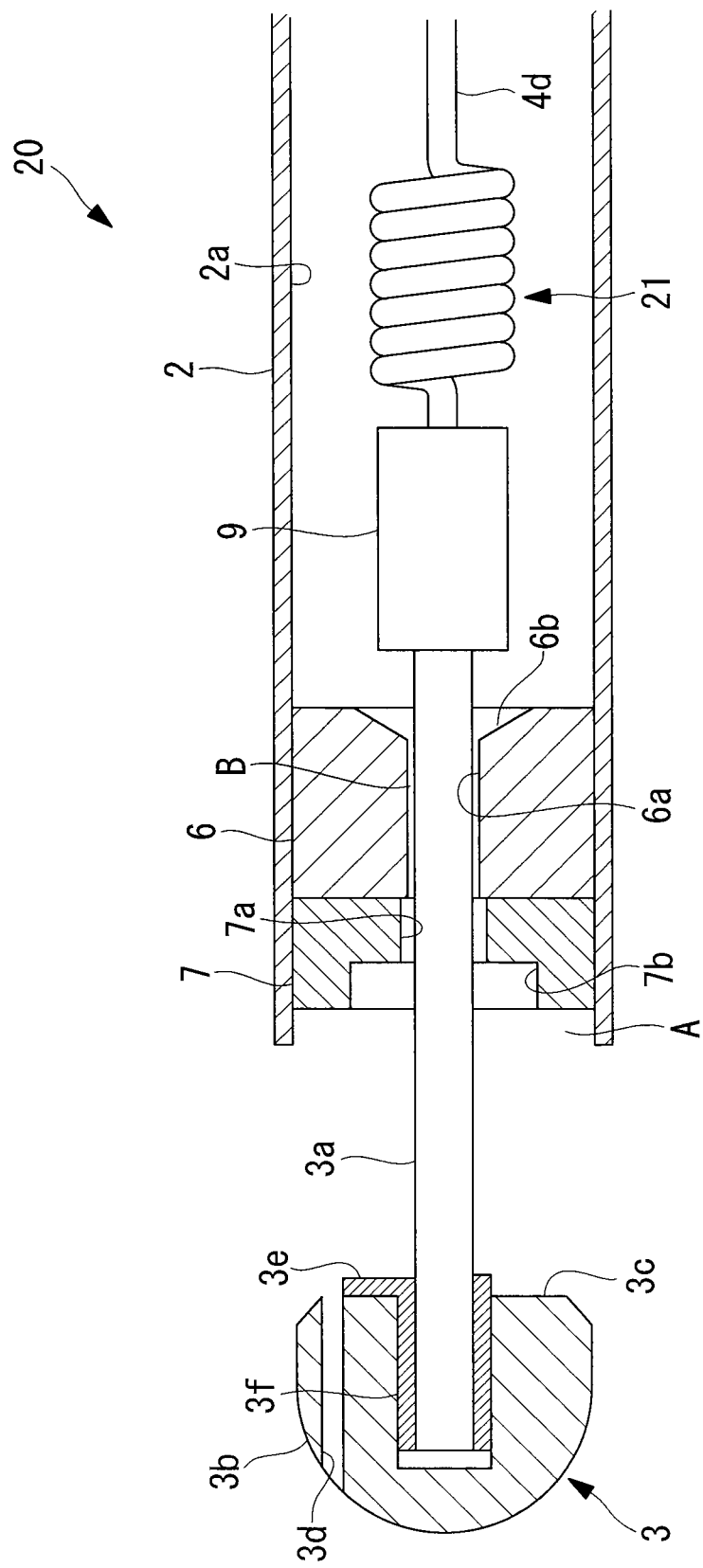
FIG. 5 is a magnified longitudinal sectional view of the distal-end portion of a high-frequency treatment instrument according to a second embodiment of the present invention.

In this embodiment, as shown in FIG. 5, the buffer member 21 is formed of a spring that connects the electrode member 3 and the wire 4d.

The buffer member 21 is a tension coil spring and has a stiffness and thereby it begins to undergo elastic deformation when a force exceeding a prescribed tensile force necessary to move the electrode member 3 acts thereon. The buffer member 21 is formed of an electrically conductive material so that the high-frequency current supplied via the wire 4d can be supplied to the electrode member 3.

The buffer member 21 is not limited to a tension coil spring, and any spring, such as a leaf spring, may be adopted.

Unlike the high-frequency treatment instrument 1 according to the first embodiment, the distal end of the sheath is not bent inward in the radial direction, and when the electrode member 3 is moved to the extreme proximal end, the sheath 2 slightly extends farther toward the distal end side than the insulating tip 7 does, so that the distal end of the sheath 2 covers the outer circumference of the large-diameter portion 3b throughout the entire circumference thereof. Accordingly, the distal end portion of the sheath 2 does not have a buffer function; however, it functions as a sealing member that seals the periphery of the space A between the insulating tip 7 and the large-diameter portion 3.

The operation of the thus-configured high-frequency treatment instrument 20 according to this embodiment will be described below.

With the high-frequency treatment instrument 20 according to this embodiment, when a tensile force is generated by moving the movable portion 4c to the proximal end side relative to the handle 4b in the operating portion 4, the generated tensile force is transmitted to the electrode member 3 via the wire 4d and the buffer member 21, and the electrode member 3 is moved towards the proximal end side. Then, the electrode member 3 abuts against the insulating tip 7, and thereby further retraction is restricted.

At this time, an impact occurs due to the collision between the large-diameter portion 3b and the insulating tip 7; however, the buffer member 21 disposed between the electrode member 3 and the wire 4d elastically deforms, and thereby the impact is reduced. In other words, an impact high enough to cause the large-diameter portion 3b to fall off the rod-shaped electrode portion 3a does not act on the large-diameter portion 3b, and it is possible to prevent it from falling off or being damaged.

The buffer member 21 should be disposed at any position between the electrode member 3 and the operating portion 4, but closer to the electrode member 3 is preferable. In other words, in the case where the sheath 2 is bent and the case where the sheath 2 is not bent, the friction acting between the wire 4d and the sheath 2 greatly differs, and therefore, if the buffer member 21 is disposed at a position closer to the operating portion 4, the wire 4d does not move due to friction between the wire 4d and the sheath 2, and the buffer member 21 presumably ends up being elastically deformed.

In contrast, by disposing the buffer member 21 closer to the electrode member 3, it is possible to elastically deform the buffer member 21 only in the case where the tensile force, which is reduced by friction, exceeds a prescribed threshold, and an advantage is afforded in that it is possible to reduce the impact at the time of a collision while allowing the electrode member 3 to be smoothly advanced and retracted.

The inventors have arrived at the following aspects of the present invention.

One aspect of the present invention provides a high-frequency treatment instrument comprising: an elongated cylindrical sheath formed of a flexible material; an electrode member that is disposed inside the sheath so as to be advanceable/retractable in a longitudinal direction thereof and to which a high-frequency current is supplied; a distal-end member that is disposed at a distal end side of the sheath and that has a through-hole through which the electrode member passes; and a liquid supply means that supplies liquid towards a front side in the longitudinal direction of the sheath via a flow path that is connected to a proximal end side of the sheath and that is formed in the sheath and via a gap between the through-hole and the electrode member, which communicates with the flow path, wherein the electrode member includes a rod-shaped electrode portion that passes through the through-hole in a movable manner, and a large-diameter portion that is provided at a distal end of the rod-shaped electrode portion, that is formed of an insulating material, and that has an outer diameter larger than an diameter of the through-hole, the large-diameter portion includes an electrode hole that passes through the large-diameter portion in the longitudinal direction, and the high-frequency treatment instrument comprises, between the distal-end member and the large-diameter portion, a buffer member which can be elastically deformed in the longitudinal direction when the electrode member is moved to the most proximal end side and which seals a periphery of a space formed between the distal-end member and the large-diameter portion throughout the entire circumference thereof, wherein the space communicates with the through-hole and the electrode hole.

According to this aspect, when the electrode member is maximally pulled into the through-hole in the distal-end member disposed at the distal end of the sheath, the space between the large-diameter portion of the electrode member and the distal-end surface of the distal-end member is sealed by the buffer member throughout the entire circumference thereof, and the gap between the electrode member and the through-hole communicates with the electrode hole in the large-diameter portion. In this state, when the liquid supply means is operated, the liquid supplied to the distal end side from the proximal end side via the flow path in the sheath is discharged straight in front of the large-diameter portion via the gap and the electrode hole. In this case, since the large-diameter portion and the distal-end member are sealed by the buffer member, the liquid supplied via the gap is discharged from the electrode hole without leaking, and it is possible to efficiently perform local injection.

On the other hand, treatment such as incision or the like of tissue inside the body using the high-frequency treatment instrument according to this aspect is performed by advancing the electrode member relative to the sheath and supplying high-frequency current to the electrode member. For example, in the state in which the large-diameter portion is placed in a hole in the mucous membrane, by moving the electrode member while supplying high-frequency current, it is possible to incise the mucous membrane with the rod-shaped electrode portion. In this case, since the large-diameter portion, which is formed of an insulating material, is in contact with the submucosal tissue when the mucous membrane is incised with the electrode member placed in the mucous membrane, the submucosal tissue is not pierced by the large-diameter portion, which is larger than the rod-shaped electrode portion, and the submucosal tissue is not burned either.

Thus, according to this aspect, even when a large force is applied to the electrode member when pulling it into the sheath or when the electrode member is repeatedly pulled in and out of the through-hole to remove tissue attached to the electrode member during treatment such as incision, the large-diameter portion does not collide with the distal-end member, and the buffer member interposed therebetween can be elastically deformed in the longitudinal direction, thus reducing the impact. As a result, it is possible to prevent the occurrence of a drawback wherein the large-diameter portion falls off the rod-shaped electrode portion or becomes damaged, due to an impact caused by the collision.

In the above-described aspect, the buffer member may be formed by making a distal end portion of the sheath protrude inward in the radial direction throughout the entire circumference thereof.

By doing so, the distal end portion of the sheath is used as the buffer member; therefore, bending processing of the distal end portion of the sheath becomes unnecessary, there is no need to use a separate component, thus reducing the number of parts, and it is possible to easily perform buffering and sealing between the large-diameter portion and the distal-end member.

In the above-described aspect, the buffer member may be formed by bending the distal end portion of the sheath inward in the radial direction throughout the entire circumference thereof.

By doing so, the buffer member is formed by bending the distal end portion of the sheath; therefore, it is not necessary to use a special object as the sheath, thus achieving cost-effectiveness, and it is possible to easily perform buffering and sealing between the large-diameter portion and the distal-end member by means of the spring force of the sheath material and a spring force that acts in a direction that restores the bending of the sheath.

Another aspect of the present invention provides a high-frequency treatment instrument comprising: an elongated cylindrical sheath formed of a flexible material; an electrode member that is disposed inside the sheath so as to be advanceable/retractable in a longitudinal direction thereof and to which a high-frequency current is supplied; a distal-end member that is disposed at a distal end side of the sheath and that has a through-hole through which the electrode member passes; an operating portion that is disposed at a proximal end side of the sheath and that is for generating a tensile force that pulls the electrode member; a tensile-force transmitting member that transmits the tensile force generated with the operating portion to the electrode member; and a liquid supply means that supplies liquid towards a front side in the longitudinal direction of the sheath via a flow path that is connected to a proximal end side of the sheath and that is formed in the sheath and via a gap between the through-hole and the electrode member, which communicates with the flow path, wherein the electrode member includes a rod-shaped electrode portion that passes through the through-hole in a movable manner, and a large-diameter portion that is provided at a distal end of the rod-shaped electrode portion, that is formed of an insulating material, and that has an outer diameter larger than an diameter of the through-hole, the large-diameter portion includes an electrode hole that passes through the large-diameter portion in the longitudinal direction, the high-frequency treatment instrument comprises, between the distal-end member and the large-diameter portion, a sealing member that seals a periphery of a space formed between the distal-end member and the large-diameter portion throughout the entire circumference thereof when the electrode member is moved to the most proximal end, the through hole communicating with the through-hole and the electrode hole, and a buffer member, between the electrode member and the operating portion, that elastically deforms in the longitudinal direction when the electrode member is moved to the most proximal end.

According to this aspect, when the tensile force generated by operating the operating portion is transmitted to the electrode member by the tensile-force transmitting member so that the electrode member is maximally pulled into the through-hole in the distal-end member disposed at the distal end of the sheath, the space between the large-diameter portion of the electrode member and the distal-end surface of the distal-end member is sealed by the sealing member throughout the entire circumference thereof, and the gap between the electrode member and the through-hole communicates with the electrode hole in the large-diameter portion. In this state, when the liquid supply means is operated, the liquid supplied to the distal end side from the proximal end side via the flow path in the sheath is discharged straight in front of the large-diameter portion via the gap and the electrode hole. In this case, since the large-diameter portion and the distal-end member are sealed by the sealing member, the liquid supplied via the gap is discharged from the electrode hole without leaking, and it is possible to efficiently perform local injection.

Thus, when a large force is applied when pulling the electrode member into the sheath or when the electrode member is repeatedly pulled in and out of the through-hole to remove tissue attached to the electrode member during treatment such as incision or the like, if the tensile force transmitted via the tensile-force transmitting member is excessively large, the buffer member is elastically deformed, and it is possible to prevent the excessively large tensile force from being directly transmitted to the electrode member. Accordingly, even if the large-diameter portion collides with the distal-end member, the buffer member is elastically deformed in the longitudinal direction, and thus it is possible to reduce the impact. As a result, it is possible to prevent the occurrence of a drawback wherein the large-diameter portion falls off the rod-shaped electrode portion or becomes damaged, due to the impact caused by a collision.

In the above-described aspect, the buffer member may be disposed between the electrode member and the tensile-force transmitting member.

By doing so, when the friction between the sheath and the tensile-force transmitting member disposed inside the sheath increases by bending of the sheath, the tensile force generated by operating the operating portion is reduced by the time it is transmitted to the electrode member. By disposing the buffer member close to the electrode member, even if the friction varies due to bending of the sheath, transmission of the tensile force by the tensile-force transmitting member and buffering by the elastic deformation of the buffer member can both be reliably achieved.

Advantageous Effects of Invention

The aforementioned aspects afford an advantage in which it is possible to prevent a large-diameter portion from falling off a rod-shaped electrode portion or being damaged, even when a large tensile force acts on a tensile-force transmitting member.

REFERENCE SIGNS LIST 1, 20 high-frequency treatment instrument
2 sheath
2a inner hole (flow path)
3 electrode member
3a rod-shaped electrode section
3b large-diameter section
3d electrode hole
4 operating portion
4d wire (tensile-force transmitting member)
5 liquid supply means
6 distal-end member
6a through-hole
10, 12, 21 buffer member
B gap

The invention claimed is:

1. A high-frequency treatment instrument comprising:
   an elongated cylindrical sheath formed of a flexible material;
   an electrode member disposed inside the sheath so as to be advanceable/retractable in a longitudinal direction of the sheath, a high-frequency current being supplied to the electrode member;
   a distal-end member disposed at a distal end side of the sheath, the distal end member having a through-hole through which the electrode member passes; and
   a liquid supply means connected to a proximal end side of the sheath, the liquid supply means supplying liquid towards the distal end side in the longitudinal direction of the sheath via a gap between the through-hole and the electrode member and via a flow path formed between the gap and the liquid supply means so as to be located in the sheath,
   wherein the electrode member includes a rod-shaped electrode portion that passes through the through-hole in a movable manner, and a large-diameter portion provided at a distal end of the rod-shaped electrode portion, the large-diameter portion being formed of an insulating material and having an outer diameter larger than a diameter of the through-hole,
   the large-diameter portion includes an electrode hole that passes through the large-diameter portion in the longitudinal direction,
   the sheath comprises a buffer member formed by making a distal end portion of the sheath protrude inward in a radial direction throughout an entire circumference of the distal end portion, the buffer member being located between the distal-end member and the large-diameter portion,
   the buffer member is configured to come into contact with the large-diameter portion when the electrode member is moved to a proximal-most end side,
   the buffer member is further configured to deform in the longitudinal direction so as to seal a periphery of a space communicating with the through-hole and the electrode hole throughout the entire circumference and to form a gap between the large-diameter portion and the distal end member when the large-diameter portion abuts against the buffer member, and
   the liquid supply means supplies the liquid toward the distal end side of the sheath via a space between the buffer member and the rod-shaped electrode portion when the large-diameter portion abuts against the buffer member.

2. The high-frequency treatment instrument according to claim 1, wherein an inner diameter of the buffer member is larger than an outer diameter of the rod-shaped electrode portion.

3. The high-frequency treatment instrument according to claim 2, wherein the buffer member is formed by bending the distal end portion of the sheath inward in the radial direction throughout the entire circumference thereof.

* * * * *